(12) United States Patent
Morén

(10) Patent No.: US 10,322,240 B2
(45) Date of Patent: Jun. 18, 2019

(54) POWER PACK LOCK

(71) Applicant: Carebay Europe Ltd, Sliema (MT)

(72) Inventor: Stefan Morén, Kista (SE)

(73) Assignee: SHL Medical AG, Zug (CH)

(*) Notice: Subject to any disclaimer, the term of this patent is extended or adjusted under 35 U.S.C. 154(b) by 929 days.

(21) Appl. No.: 14/902,145

(22) PCT Filed: Mar. 12, 2014

(86) PCT No.: PCT/EP2014/054903
§ 371 (c)(1),
(2) Date: Dec. 30, 2015

(87) PCT Pub. No.: WO2014/154491
PCT Pub. Date: Oct. 2, 2014

(65) Prior Publication Data
US 2016/0303327 A1 Oct. 20, 2016

(30) Foreign Application Priority Data
Mar. 25, 2013 (SE) .................................. 1350374

(51) Int. Cl.
*A61M 5/315* (2006.01)
*A61M 5/20* (2006.01)
(Continued)

(52) U.S. Cl.
CPC ...... *A61M 5/31501* (2013.01); *A61M 5/2033* (2013.01); *A61M 5/24* (2013.01); *A61M 5/31571* (2013.01); *A61M 5/31578* (2013.01); *A61M 5/3204* (2013.01); *A61M 2005/2013* (2013.01); *A61M 2005/2073* (2013.01);
(Continued)

(58) Field of Classification Search
CPC .. A61M 2005/2073; A61M 2005/2013; A61M 2005/3142; A61M 2005/208; A61M 5/31501; A61M 5/31571; A61M 5/31578; A61M 5/31; A61M 5/2033; A61M 5/3272; A61M 5/3232; A61M 5/24; A61M 5/3204; A61M 5/20
See application file for complete search history.

(56) References Cited

U.S. PATENT DOCUMENTS

| 5,865,795 A * | 2/1999 | Schiff ...................... A61M 5/30 604/68 |
| 2005/0261634 A1* | 11/2005 | Karlsson ................. A61M 5/20 604/197 |

FOREIGN PATENT DOCUMENTS

| GB | 2477487 A * | 8/2011 | .......... A61M 5/2033 |
| GB | 2477487 A | 8/2011 | |

(Continued)

*Primary Examiner* — Kami A Bosworth
*Assistant Examiner* — Alexandra Lalonde
(74) *Attorney, Agent, or Firm* — McDonnell Boehnen Hulbert & Berghoff LLP

(57) ABSTRACT

A medicament delivery device includes a proximal sub-assembly and a distal sub-assembly configured to be connected to each other. The proximal sub-assembly includes a key member, and the distal sub-assembly includes a power pack unit having a lock mechanism for locking the power pack unit such that unintentional activation of the power pack unit during transportation is avoided. The key member is configured to interact with the lock mechanism during assembling of the proximal and distal sub-assemblies such that the lock mechanism is released.

16 Claims, 6 Drawing Sheets

(51) Int. Cl.
*A61M 5/32* (2006.01)
*A61M 5/24* (2006.01)
*A61M 5/31* (2006.01)

(52) U.S. Cl.
CPC ............... *A61M 2005/3125* (2013.01); *A61M 2005/3142* (2013.01)

(56) References Cited

FOREIGN PATENT DOCUMENTS

| WO | 2010/076569 A1 | 7/2010 |
| WO | 2010/125400 A2 | 11/2010 |
| WO | 2012/073032 A1 | 6/2012 |
| WO | 2012/116687 A1 | 9/2012 |

\* cited by examiner

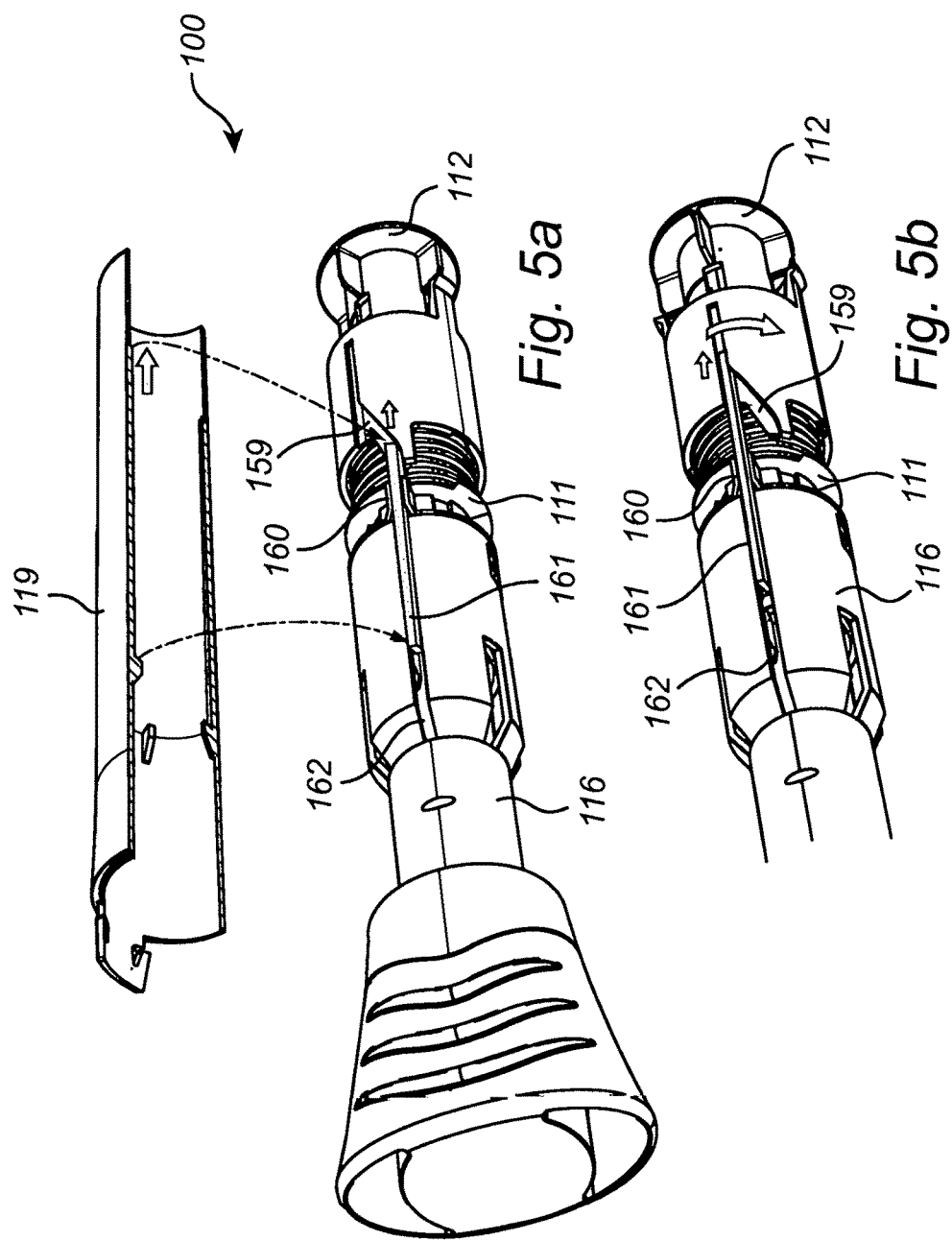

POWER PACK LOCK

CROSS-REFERENCE TO RELATED APPLICATIONS

This is the National stage filing under 35 U.S.C. 371 of the International Application PCT/EP2014/054903 filed Mar. 12, 2014 which claims benefit under 35 U.S.C 119 (a-d) to SE1350374-3 filed Mar. 25, 2013.

FIELD OF THE INVENTION

The present invention relates to a medicament delivery device comprising a power pack unit having a transport lock mechanism.

BACKGROUND OF THE INVENTION

The invention concerns auto injectors having separable front and rear housings where the front housing is arranged to receive and hold a container subassembly, such as a syringe, and the rear housing comprises a power pack unit arranged to act on a plunger in the container subassembly such that a medicament can be expelled. WO-2010/076569 discloses an injector in which a delivery member cover can be locked against retraction such that the delivery member is not exposed. This provides for a certain degree of user friendliness and safety. However, the arrangement of that prior art has a drawback in that the power pack unit may unintentionally be released. If a user, for some reason, pushes the firing button, the plunger rod will be released and fly off due to the force of the main drive spring, which may be rather strong. Since in many cases, the front part and the rear part are provided by one supplier and the container part is provided by another supplier and final assembly of these parts is done by a third part prior to reaching an end consumer, it is of utmost importance that the different parts are delivered in a "ready-to-assemble" condition. The power pack unit might however be unintentionally released during handling or transportation, thereby releasing a plunger rod. This is first of all dangerous since the forces involved are considerable; secondly it requires quite an amount of extra work to re-assemble the power pack unit.

SUMMARY OF THE INVENTION

It is therefore an object of the invention to provide a medicament delivery device with improved qualities. In particular, it is an object of the present invention to provide a medicament delivery device in which the power pack unit has improved safety properties. This object and other objects are solved by an injection device as defined in claim 1. Preferred embodiments of the present invention are defined in the dependent claims.

Thus, in accordance with an aspect of the present invention, there is provided a medicament delivery device comprising a proximal sub-assembly and a distal sub-assembly configured to be connected to each other, wherein the proximal sub-assembly comprises a key member and wherein the distal sub-assembly comprises a power pack unit having a transport lock mechanism for transport locking said loaded power pack unit such that unintentional activation of said loaded power pack unit during transportation is avoided, and wherein said key member is configured to interact with said lock mechanism during assembling of said proximal and distal sub-assemblies such that said transport locking is released. The key member is arranged on the inner surface of a housing which is part of the proximal sub-assembly and which is configured to encase said distal sub-assembly.

In accordance with an embodiment of the present invention, the power pack unit comprises an actuator, an actuator sleeve arranged to at least partially encompass said actuator, a plunger rod being axially moveable in said actuator, a first biasing member being arranged in the actuator for driving said plunger rod, and a rear end cover being coupled to the actuator and arranged to at least partially encompass said actuator and said actuator sleeve, and wherein said rear end cover and said actuator are rotatable fixed relative to each other and axially moveable relative to each other.

This has the advantage that the power pack unit can be kept in a locked position until a final assembly has been done such that the biased plunger rod cannot be unintentionally released. The first biasing spring typically has an uncompressed length of about 250 mm and it is then compressed to about 80 mm such that an unintentional release of the plunger rod could cause serious injury to a user and in all events it is very inconvenient.

In accordance with an embodiment of the present invention, the transport lock mechanism comprises a protruding element arranged on said actuator and a securing compartment arranged on said actuator sleeve wherein the protruding element is releasably accommodated within said securing compartment such that relative axial movement between said actuator and said actuator sleeve is prevented during transportation. This provides for a reliable and yet safe securing of the actuator relative to the actuator sleeve.

In accordance with an embodiment of the present invention, the actuator sleeve and the actuator are rotatably displaceable relative each other between a locked position, in which the actuator and the actuator sleeve are axially fixed relative to each other by the transport locking mechanism, and a released position, in which the actuator and the actuator sleeve can be axially moveable relative to each other.

In accordance with an embodiment of the present invention, the actuator sleeve comprises a first guide member having a longitudinal direction extending generally in parallel to the key member and configured to interact with said key member, such that, when said proximal and distal subassemblies are connected to each other, said actuator sleeve is slidable in relation to said housing but rotationally locked to said housing.

In accordance with an embodiment of the present invention, the rear end cover comprises a second guide member having a longitudinal but inclined direction in relation to the key member followed by a longitudinal direction extending generally in parallel to the key member and configured to interact with said key member, such that, when said proximal and distal sub-assemblies are connected to each other, said rear end cover is rotatable in relation to said housing, and thus also in relation to the actuator sleeve so that the actuator is rotated in relation to the actuator sleeve whereby the transport lock mechanism is released. This arrangement provides for an automatic arming of the power pack unit. This since the actuator and the actuator sleeve will be forced to rotate to assume their released position upon insertion of the power pack unit into the housing.

In accordance with an embodiment of the present invention, the first and the second guide members are grooves and wherein the key member is a rib extending in a longitudinal direction of the housing.

In accordance with an embodiment of the present invention, the actuator sleeve comprises a slot which extends generally parallel to a longitudinal axis of the plunger rod and allows for a certain degree of freedom of relative axial movement between the actuator and the actuator sleeve, and wherein a part of the slot extends generally perpendicular to said slot forming said securing compartment.

In accordance with an embodiment of the present invention, a shoulder extends from a distal wall of the securing compartment. This shoulder provides additional safety against unintentional release of the plunger rod In accordance with an embodiment of the present invention, the actuator comprises a retaining member configured to interact with a mating retaining part on the plunger rod when the actuator sleeve is coaxially surrounding said retaining member and when the actuator and the actuator sleeve are in said locked and released position such that the plunger rod is secured in a distal end position from axial movement relative the actuator.

In accordance with an embodiment of the present invention, the actuator sleeve, when the actuator and the actuator sleeve are in said released position, is axially moveable relative to the actuator between a first position, in which the plunger rod is secured in said distal end position, and a second position, in which the actuator releases the plunger rod.

In accordance with an embodiment of the present invention, the inclined groove is arranged on the cylindrical surface of the rear end cover and the inclined groove has a helical shape over at least a part of its length. The provision of a helical groove allows for fine tuned properties of the arming process since the pitch of the helical groove determines the necessary length of the groove and the force necessary to bring the actuator and the actuator sleeve to their released position. A coarse pitch requires the groove to have a more extended length than a fine pitch would but requires on the other hand a reduced effort.

In accordance with an embodiment of the present invention, the retaining member is radial outwardly biased. The biasing ensures that as soon as the actuator sleeve assumes its second position, the plunger rod is released.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCIRPTION OF THE DRAWINGS

The invention will now be described in more detail and with reference to the appended drawings in which:

FIGS. 5a and 5b are schematic perspective views of a power pack unit of the medicament delivery device according to the invention.

DESCRIPTION OF PREFERRED EMBODIMENTS

Figure 1:
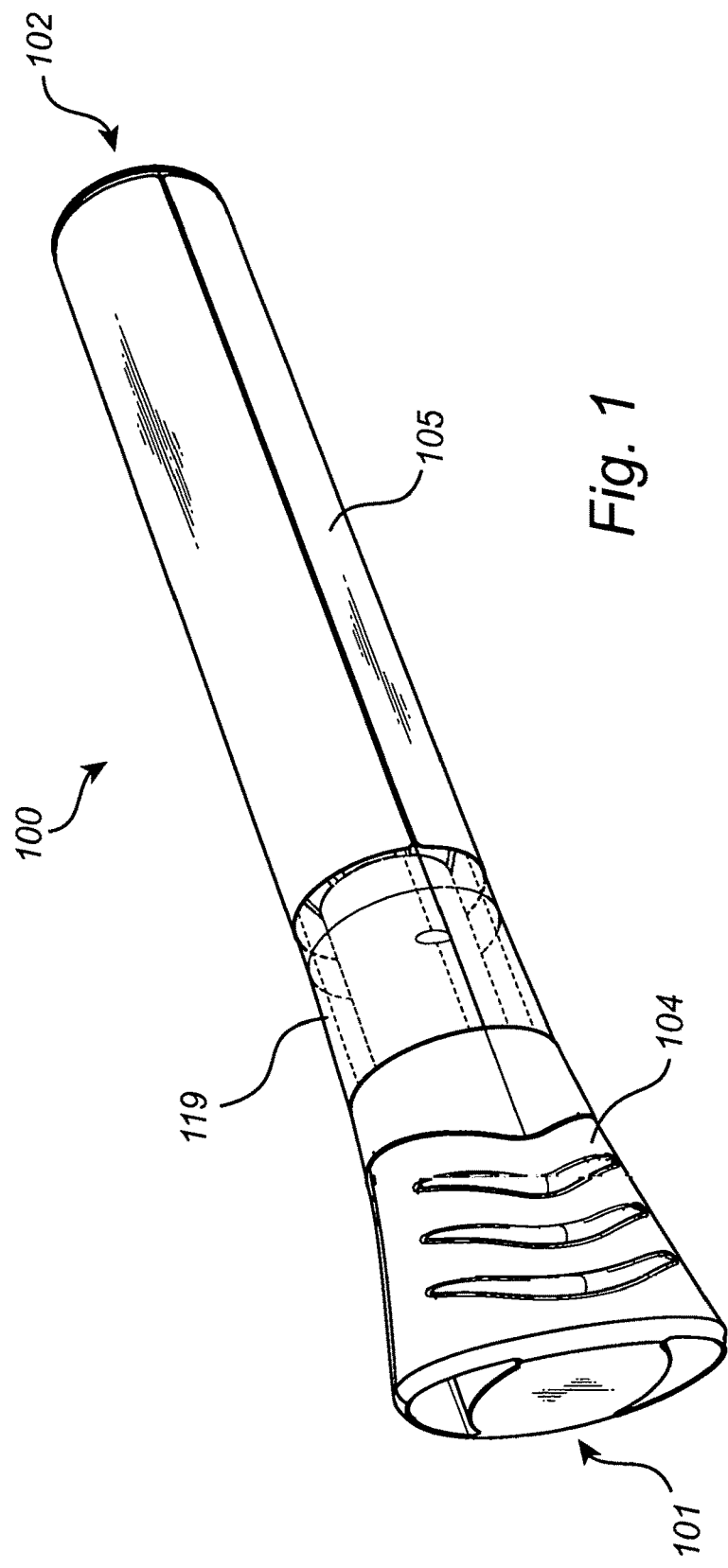
FIG. 1 is a schematic perspective view of an embodiment of the medicament delivery device according to the invention.

In a first embodiment of a medicament delivery device 100 according to the invention, as shown in FIG. 1, a medicament delivery device 100 having a proximal end 101 and a distal end 102 is provided. Concerning the terms "distal" and "proximal" they refer to points which are further away and closer to the injection site respectively. The medicament delivery device 100 comprises a housing 119 made from e.g. thermoplastic, a front cap 104, also made from thermoplastic or similar, and a label 105.

Figure 2:
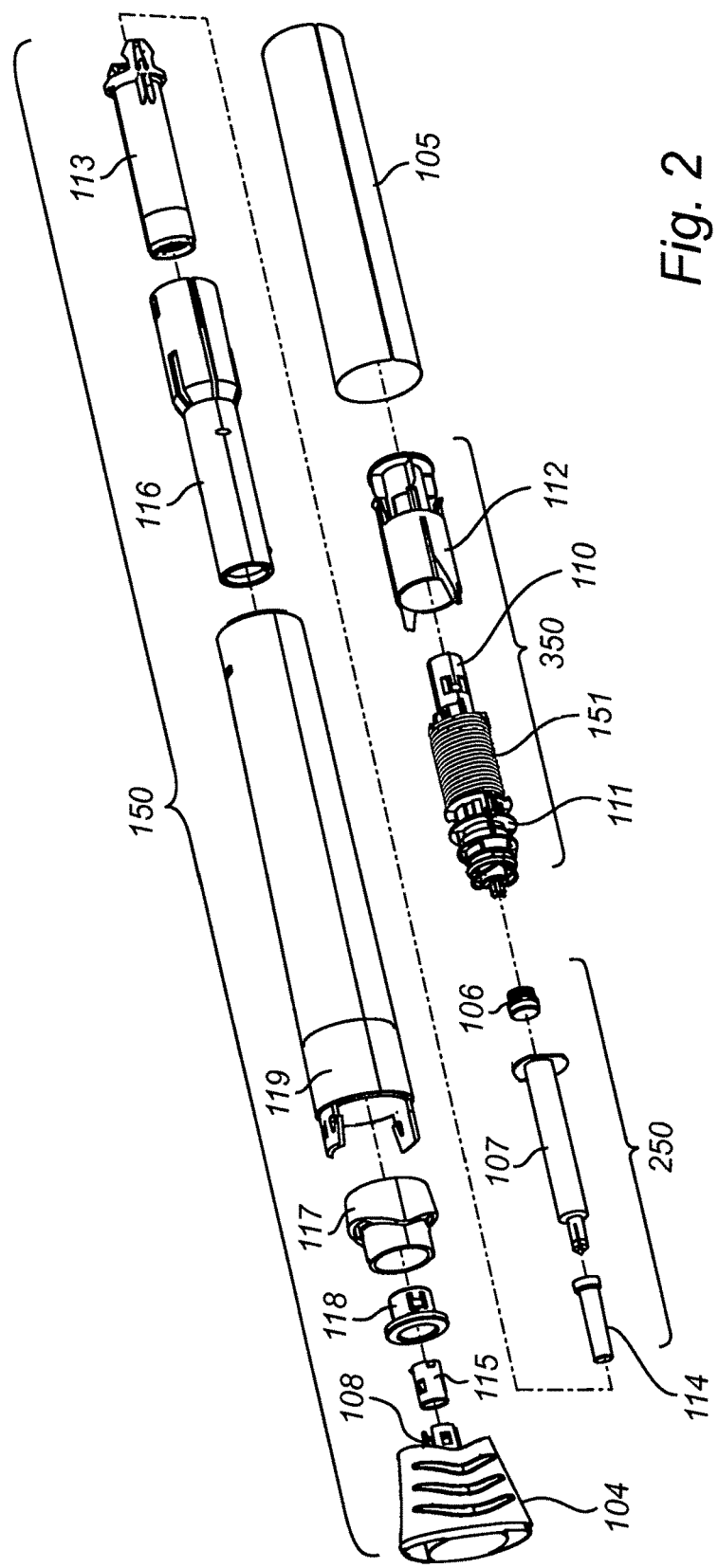
FIG. 2 is a schematic exploded perspective view of an embodiment of the medicament delivery device according to the invention.

The building up of a medicament delivery device 100 according to the invention will now be described, referring first to FIG. 2. FIG. 2 shows an exploded perspective view of a first embodiment of the medicament delivery device 100 in accordance with the present invention. The medicament delivery device 100 generally comprises a proximal sub-assembly 150, 250 and a distal sub-assembly 350 configured to be connected to each other. This means that during the final assembly of the medicament delivery device according to the present invention, these two sub-assemblies are assembled and a label 105 having information related to the medicament is attached to the housing 119. The label 105 could be provided with grip enhancing materials.

Turning first to the distal sub-assembly 350, this comprises a power pack unit having a transport lock mechanism for transport locking said power pack unit such that unintentional activation of said power pack unit during transportation is avoided. The power pack unit comprises an actuator 110, an actuator sleeve 111 arranged to at least partially encompass said actuator 110, a plunger rod 109 being axially moveable in said actuator 110, a first biasing member 152 being arranged in the actuator 110 for driving said plunger rod 109, and a rear end cover 112 being coupled to the actuator 110 and arranged to at least partially encompass said actuator 110 and said actuator sleeve 111, and wherein said rear end cover 112 and said actuator 110 are rotatable fixed relative to each other and axially moveable relative to each other.

Further, the proximal sub-assembly comprises a key member 161 and is configured to interact with said lock mechanism during assembling of said proximal and distal sub-assemblies such that said transport lock is released as will be discussed in detail below. The key member 161 is arranged on the inner surface of the housing 119 which is part of the proximal sub-assembly and wherein said housing 119 is configured to encase said distal sub-assembly. The proximal sub-assembly further comprises a container part 250, a container sleeve 113, a delivery member cover or activation member 116, a front end cover 117, a front ring 118 and a cap sub-assembly.

In the present embodiment, the housing 119 is provided with two key members 161, here represented by two elongated ribs, extending along the inner surface thereof, preferably at diametrically opposed positions and they are intended to interact with means on the delivery member cover 116 as the housing 19 is slipped onto the delivery member cover 116. In FIG. 5a, an axial position of the housing 119 is indicated corresponding to when the housing 119 is partly slipped onto the delivery member cover 116 and the key member 161 slides in a guide member 162, here represented by two elongated grooves extending along the outer surface of the delivery member cover 116 and preferably at diametrically opposed positions. Thus, the delivery member cover 116 and the housing 119 are prevented from rotational movement relative to each other.

Further, the delivery member cover 116 is movable arranged within said housing 119 and within the delivery member cover 116, in turn, is a container sleeve 113 arranged to receive and hold the container 107. A front end cover 117 is provided at a proximal end of housing 119 and is held in place by means of a snap-fit connection provided by connecting elements 120 at a proximal end of the housing 119 and corresponding connecting elements within the front end cover 117. The front ring 118 is arranged and fixed to the delivery member cover 116 at a proximal end thereof after the front end cover 117 is mounted at a proximal end of housing 119 and the housing 119 is slipped onto the delivery member cover 116.

The container 107, typically having a glass medicament container, is normally not rigidly mounted within the container sleeve 113. The container part 250 comprises a container 107 within which a plunger 106 is arranged and a delivery member, here represented by a needle, is arranged at a proximal end of the container 107. In order to protect the delivery member and ensure sterility of the delivery member, a delivery member shield 114, here represented by a needle shield, is arranged on the delivery member.

The cap sub-assembly comprises a front cap 104 having a shield grabber support 108 into which shield a shield grabber 115 can be inserted. The front cap 104 comprises a shield grabber support 108 arranged to receive and hold a shield grabber 115. Shield grabber 115 has a generally circular cross-section and dimensioned to fit within shield grabber support 108 and the fit should be such that the shield grabber 115 can move axially relative the shield grabber support 108. An excessively tight fit is therefore unwanted since this could prevent or at least hamper the axial movement of the shield grabber 115 relative to the shield grabber support. A certain amount of radial play between the shield grabber 115 and the shield grabber support 108 is acceptable but it should be restricted in order to prevent the shield grabber 115 from wedging and getting stuck within the shield grabber support 108. The shield grabber 115 further comprises a plurality of inwardly folded hook element in the form of tabs being cut and folded inwardly from the shield grabber casing. These tabs are each provided with a pointed tip for interacting with the delivery member shield 114 of the container 107 and function as barbs. These tabs will slide over the outer surface of the delivery member shield 114 when the front cap 104 is moving in a direction from a proximal end towards a distal end, e.g. during mounting to the front end cover 117 which is already connected to the housing 119 and wherein the delivery member cover 116 and the container 107 together with the container sleeve 113 are already mounted within the housing 119, but as soon as the front cap 104, and thus the shield grabber 115 is moved towards a proximal position the tabs will cut into the delivery member shield 114. Therefore, the delivery member shield 114 can be loosened from the delivery member by axially pulling and/or rotating the front cap 104. Preferably, the shield grabber 115 is made from metal which ensures light weight, and sufficient rigidity of the shield grabber 115.

Figure 3:
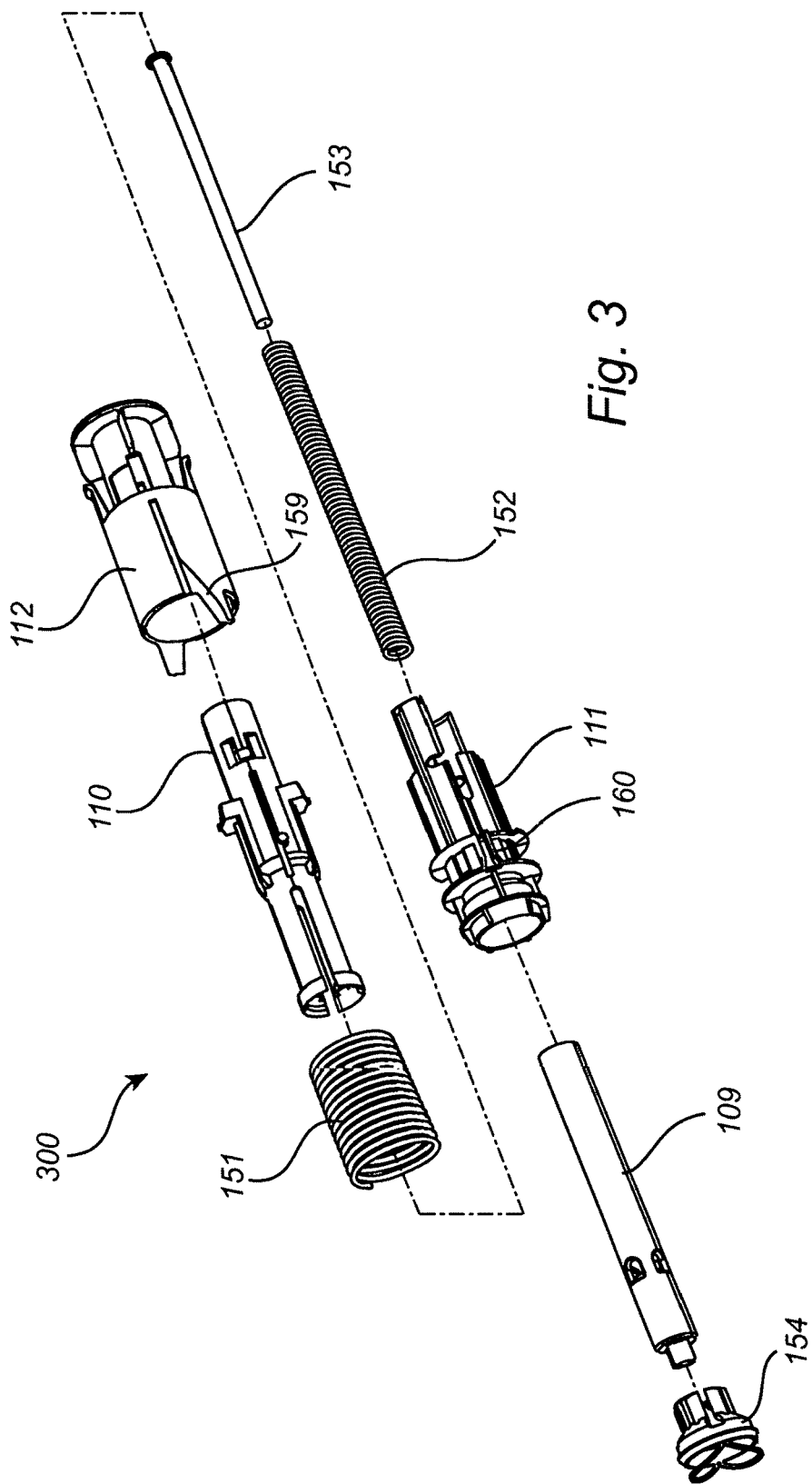
FIG. 3 is a schematic exploded perspective view of a power pack unit of the medicament delivery device according to the invention.

The power pack unit according to the present invention will now be described, referring generally to FIG. 3. The plunger rod 109 is arranged to act upon and drive the plunger 106 arranged within the container 107. The plunger rod 109 is biased by the first biasing member 152, here represented by a first spring. A support rod 153 is provided within the first spring 152 in order to prevent the first spring 152 from buckling within actuator 110. The plunger rod is hollow and the first spring is arranged between an inner transversal wall surface positioned at the proximal end of the plunger rod and an inner transversal wall surface positioned at the distal end of the actuator 110. The power pack unit further comprises a second biasing member 151 and a container holder 154. The actuator 110 is, in turn, arranged at least partly within the actuator sleeve 111 and the actuator 110 and the actuator sleeve 111 are biased by the second biasing member 151, here represented by a second spring, biasing the actuator 110 towards a distal end and the actuator sleeve 111 towards a proximal end. The second biasing member is arranged between radial outwardly protruding ledges on the outer surface of the actuator 110 and radial outwardly protruding ledges on the outer surface of the actuator sleeve. The rear end cover 112 is arranged to at least partly encompass the actuator 110 and the actuator sleeve 111. The container holder 154 is arranged at a proximal end of plunger rod 109 and is configured to interact with the container sleeve 113 for holding the container sleeve in place within the delivery device.

Figure 4A:
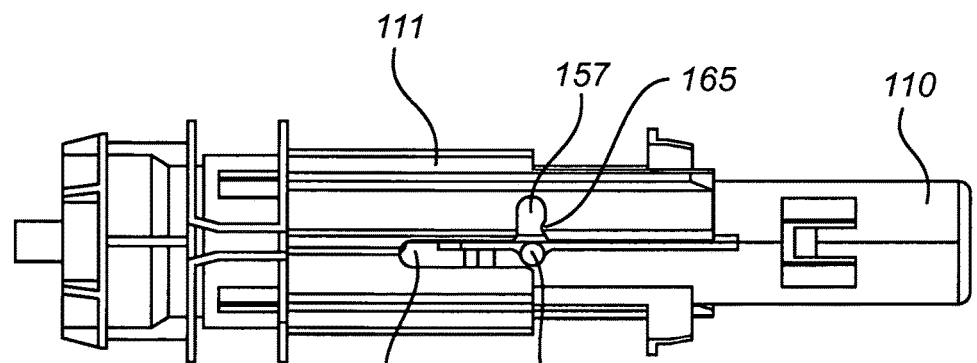
FIGS. 4a and 4b are schematic perspective views of parts of a power pack unit of the medicament delivery device according to the invention.
Figure 4B:
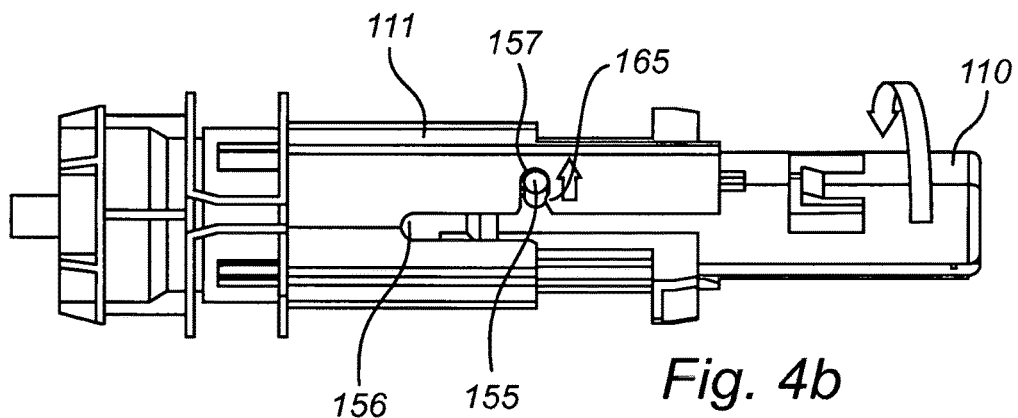

Turning now to FIGS. 4a and 4b, the transport lock mechanism comprises a protruding element 155 arranged on said actuator 110 and a securing compartment 157 arranged on said actuator sleeve 111. Further, the actuator sleeve 111 comprises a slot 156 which extends generally parallel to a longitudinal axis of the plunger rod 109 and allows for a certain degree of freedom of relative axial movement between the actuator 110 and the actuator sleeve 111. A part of the slot extends generally perpendicular to the slot 156 forming said securing compartment 157. A shoulder 165 is provided on a distal wall of the compartment 157. This shoulder acts as an additional safety means. The protruding element 155 is releasably accommodated within said securing compartment 157 such that relative axial movement between said actuator 110 and said actuator sleeve 111 is prevented during transportation. The actuator sleeve 111 and the actuator 110 are rotatably displaceable relative each other between a locked position (FIG. 4b), in which the actuator 110 and the actuator sleeve 111 are axially fixed relative to each other by the transport locking mechanism, and a released position (FIG. 4a), in which the actuator 110 and the actuator sleeve 111 can be axially moveable relative to each other.

In the locked position, the protruding element 155 provided on the actuator 110 is positioned within compartment 157. In this position, the actuator 110 and the actuator sleeve 111 are prevented from axial movement relative to each other which, as will be discussed referring to FIGS. 6a and 6b below, prevents the plunger rod 109 from moving axially. The second spring 151 urges the protruding element 155 against the distal wall of the compartment 157 and in order to arrive at the released position of the actuator 110 and actuator sleeve 111, the protruding element 155 has to slide past the shoulder 165 while overcoming the force of second spring 151. As the actuator 110 and the actuator sleeve 111 rotates relative each other to the position shown in FIG. 4b, the protruding element 155 exits the compartment 157, passing shoulder 165, and the actuator 110 and actuator sleeve 111 are now free to move axially relative to each other and the power pack unit is armed and ready to release the biased plunger rod 109.

Referring to FIGS. 5a and 5b, the function of the automatic arming of the power pack unit will be explained. FIGS. 5a and 5b show a power pack unit where the housing 119 has been lifted away for reasons of better understanding.

The actuator sleeve 111 comprises a first guide member 160, here represented as a groove, having a longitudinal direction extending generally in parallel to the key member. In the present embodiment the actuator sleeve 111 is provided with two first guide members 160 preferably at diametrically opposed positions. The rear end cover 112 comprises a second guide member 159 arranged on its cylindrical surface, here represented as a groove, and having a longitudinal but inclined direction in relation to the key member 161 followed by a longitudinal direction extending generally in parallel to the key member. In the present embodiment the rear end cover 112 is provided with two second guide members 159 preferably at diametrically opposed positions. The inclined groove has a helical shape over at least a part of its length. The provision of a helical groove allows for fine-tuned properties of the arming process since the pitch of the helical groove determines the necessary length of the groove and the force necessary to bring the actuator and the actuator sleeve to their released position. A coarse pitch requires the groove to have a more extended length than a fine pitch would but requires on the other hand a reduced effort.

In the present embodiment, the housing 119 is provided with two key members 161, here represented by two elongated ribs, extending along the inner surface thereof, preferably at diametrically opposed positions. These two key members 161 are intended to interact with the first and second guide members as the proximal sub-assembly is slipped onto the distal sub-assembly towards a final assembled position of the delivery device. One of these key members 161 has in FIGS. 5a and 5b been isolated from the housing 119 and is indicated as if the housing 119 was in place encompassing the power pack unit. In FIG. 5a, an axial position of the housing 119 is indicated corresponding to when the housing 119 is partly slipped onto the power pack unit and the key member 161 slides in the first 160 and second 159 guide members arranged at the actuator sleeve 111 and the rear end cover 112 respectively. In FIG. 5a, the key member 161 of housing 119 runs through the first guide member 160 of the actuator sleeve 111 and has just reached the inclined part of the second guide member 159 of the rear end cover 112. As the housing 119 is further axially moved towards a distal end of the power pack unit, the key member 161 and the inclined part of the second guide member 159 will force the rear end cover 112 to rotate relative to the housing 119. And since the first guide members 160 of the actuator sleeve 111 extend generally parallel to the longitudinal axis of the housing 119, the actuator sleeve 111 is prevented from rotational movement relative to the housing. The rear end cover 112 is connected to the actuator 110 such that any relative rotational movement between each other is prevented but it allows for a certain amount of relative axial movement. The distal part of the actuator 110 has a key shape that fits into a corresponding inner space of the rear end cover such that any relative rotational movement between each other is prevented but it allows for a certain amount of relative axial movement. This means that as the rear end cover 112, as a consequence of the axial movement of housing 119 during assembly, rotates relative to the housing 119, delivery member cover 116 and actuator sleeve 111. The actuator 110 also rotates relative to these three elements, thus bringing the actuator 110 and the actuator sleeve 111 to their released position as indicated in FIG. 4a. The power pack unit can therefore be held in a transport locked, or un-armed, state until and during the final assembly. Only after completion of the final assembly the transport lock mechanism is released and there is no risk that an assembly worker forgets or overlooks this. When the transversal wall of the rear end cover 112 reaches the distal end of the housing 119, i.e. the transversal wall of the rear end cover is flush with the distal end of the housing; both the rear end cover 112 and the actuator 110 have rotated in relation to the housing such that the transport lock mechanism is released, i.e. the actuator 110 and the actuator sleeve 111 are in their released position as indicated in FIG. 4a. The protruding element 155 has exited the compartment 157 and passed the shoulder 165. The actuator 110 and actuator sleeve 111 are now free to move axially relative to each other. The power pack unit is armed and ready to release the biased plunger rod 109. The housing 119 further comprises an engaging member, here represented by two indentations, configured to receive a corresponding engaging member of the rear end cover 112. In the present embodiment, the corresponding engaging member of the rear end cover 112 is represented by two flexible tongues, wherein each tongue has a radial outwardly extending protrusion. Thus, when the transversal wall of the rear end cover 112 reaches the distal end of the housing 119, the radial outwardly extending protrusions of the tongues of the rear end cover 112 engage with the indentations of the housing whereby a final assembled medicament delivery device is obtained.

Figure 6A:
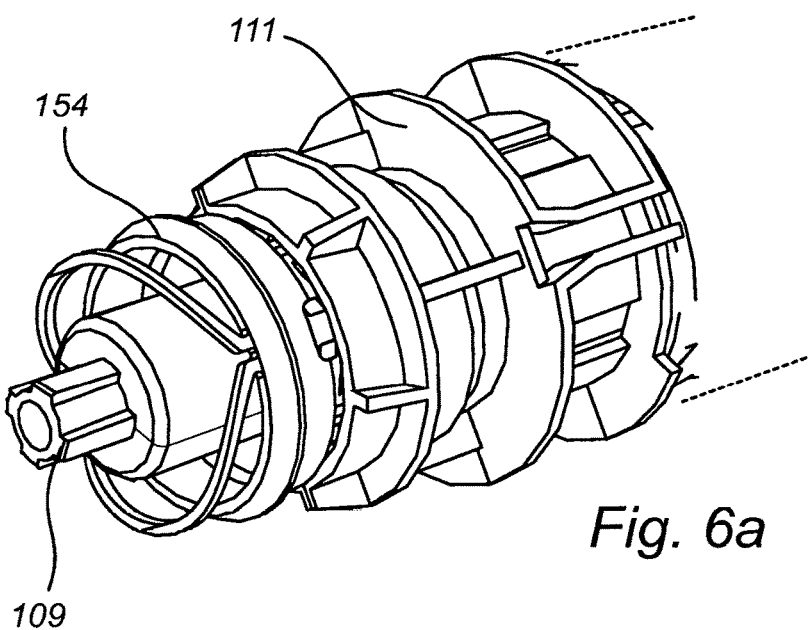
FIGS. 6a and 6b are schematic perspective views of a power pack unit of the medicament delivery device according to the invention.
Figure 6B:
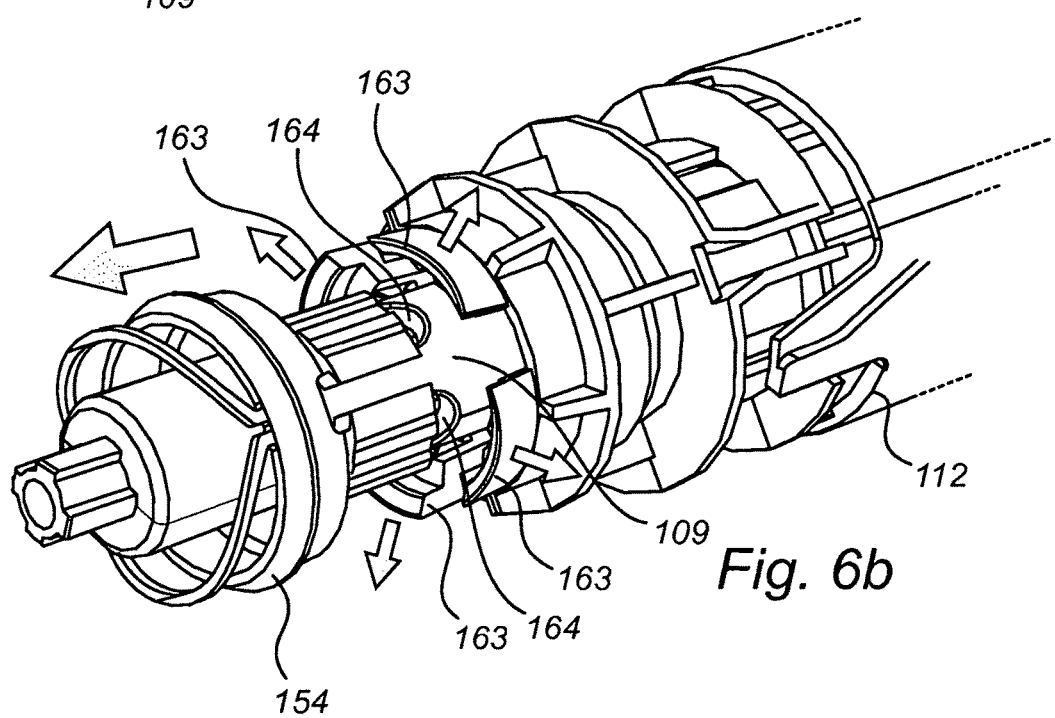

Referring to FIGS. 6a and 6b, the actuator 110 comprises a retaining member 163 configured to interact with a mating retaining 164 part on the plunger rod 109 when the actuator sleeve is coaxially surrounding said retaining member and when the actuator 110 and the actuator sleeve 111 are in said locked and released position such that the plunger rod 109 is secured in a distal end position from axial movement relative the actuator 110. The retaining member 163 is radial outwardly biased. When the actuator 110 and the actuator sleeve 111 are in said released position, the actuator sleeve 111 is axially moveable relative to the actuator 110 between a first position, in which the plunger rod 109 is secured in said distal end position, and a second position, in which the actuator 110 releases the plunger rod 109. When the actuator sleeve 111 is in said second position, the retaining member 163 of the actuator 110 flexes radial outwardly and disengages from the mating retaining 164 part on the plunger rod 109.

The front ring 118 comprises a flange at a proximal end thereof which, in a mounted state of the medicament delivery device 100, is arranged at a distance from a proximal end surface of the front end cover 117. When a user intends to perform a delivery of medicament, the medicament deliver device 100 according to the invention is triggered by pushing the front ring 118 against a preferred part of the body. This will cause the front ring 118 to be axially displaced relative to the front end cover 117 until the front ring 118 reaches the proximal end surface of the front end cover 117. During this displacement, the delivery member cover 116 will be simultaneously displaced and will bring the actuator sleeve 111 with it in its movement in a direction towards the distal end 102 of the medicament delivery device 100. Since the actuator sleeve 111 and actuator 110 have been automatically placed in their released position, relative axial movement of the actuator sleeve 111 relative to the actuator 110 is possible. As the actuator sleeve 111 moves towards the distal end of the medicament delivery device 100 the retainment members 163 provided on the proximal end of the actuator 110 disengages from corresponding engagement means 164 provided on the plunger rod 109, thus releasing the biased drive plunger rod 109 such that the medicament in container 107 can be expelled through the delivery member thereof.

Finally, it is realized that the automatic arming of the power pack unit during the final assembly of the device, i.e. when the proximal sub-assembly and the distal sub-assembly are assembled, allows for the power pack unit to be set in a secured un-armed condition at all times up until, and during, final assembly. This reduces the risk of an unintentional release of the biased plunger rod during handling of the power pack unit which, apart from being inconvenient, could possibly be dangerous to anybody handling the power pack unit. The first biasing member is typically about 250 mm in an uncompressed state and is then compressed to about 80 mm such that the force it exerts on the plunger rod is considerable.

The medicament delivery device 100 according to the shown embodiment is an auto-injector.

It is to be understood that the embodiments described above and in the drawings are to be regarded only as non-limiting examples of the invention and that they may be modified in many ways within the scope of the claims.

The invention claimed is:

1. A medicament delivery device, comprising a proximal sub-assembly and a distal sub-assembly configured to be connected to each other, wherein the proximal sub-assembly comprises a key member, and the distal sub-assembly comprises a power pack unit having a lock mechanism for transport locking the power pack unit such that unintentional activation of the power pack unit during transportation is avoided, and the key member is configured to interact with the lock mechanism during assembling of the proximal and distal sub-assemblies such that the transport locking is released, and the key member is arranged on an inner surface of a housing which is part of the proximal sub-assembly and which is configured to encase the distal sub-assembly, and the power pack unit comprises:
   an actuator,
   an actuator sleeve arranged to at least partially encompass the actuator,
   a plunger rod axially able in the actuator,
   a first biasing member arranged in the actuator for driving the plunger rod, and
   a rear end cover coupled to the actuator and arranged to at least partially encompass the actuator and the actuator sleeve, wherein the rear end cover and the actuator are rotationally fixed relative to each other and axially movable relative to each other, and
   the lock mechanism comprises a protruding element on the actuator and a securing compartment on the actuator sleeve, and the protruding element is configured to be releasably accommodated within the securing compartment such that relative axial movement between the actuator and the actuator sleeve is prevented during transportation.

2. The medicament delivery device of claim 1, wherein the actuator sleeve comprises a slot extending approximately parallel to a longitudinal axis of the plunger rod and permitting relative axial movement between the actuator and the actuator sleeve, and a part of the slot extending approximately perpendicular to a slot forming the securing compartment.

3. The medicament delivery device of claim 1, wherein the actuator sleeve and the actuator are configured to be rotationally displaceable relative to each other between a locked position, in which the actuator and the actuator sleeve are axially fixed relative to each other by the lock mechanism, and a released position, in which the actuator and the actuator sleeve are axially movable relative to each other.

4. The medicament delivery device of claim 3, wherein the actuator sleeve comprises a slot extending approximately parallel to a longitudinal axis of the plunger rod and permitting relative axial movement between the actuator and the actuator sleeve, and a part of the slot extending approximately perpendicular to a slot forming the securing compartment.

5. The medicament delivery device of claim 3, wherein the actuator sleeve comprises a first guide member having a longitudinal direction extending generally in parallel to the key member and being configured to interact with the key member, such that when the proximal and distal sub-assemblies are connected to each other, the actuator sleeve is slidable in relation to the housing but rotationally locked to the housing.

6. The medicament delivery device of claim 5, wherein the first guide member includes a groove, and the key member is a rib.

7. The medicament delivery device of claim 5, wherein the actuator sleeve comprises a slot extending approximately parallel to a longitudinal axis of the plunger rod and permitting relative axial movement between the actuator and the actuator sleeve, and a part of the slot extending approximately perpendicular to a slot forming the securing compartment.

8. The medicament delivery device of claim 5, wherein the rear end cover comprises a second guide member having a longitudinal direction inclined in relation to the key member followed by a longitudinal direction extending generally in parallel to the key member and configured to interact with the key member, such that when the proximal and distal sub-assemblies are connected to each other, the rear end cover is rotatable in relation to the housing and the actuator sleeve such that rotating the actuator in relation to the actuator sleeve releases the lock mechanism.

9. The medicament delivery device of claim 8, wherein the first and second guide members are grooves, and the key member is a rib.

10. The medicament delivery device of claim 8, wherein the actuator sleeve comprises a slot extending approximately parallel to a longitudinal axis of the plunger rod and permitting relative axial movement between the actuator and the actuator sleeve, and a part of the slot extending approximately perpendicular to a slot forming the securing compartment.

11. The medicament delivery device of claim 10, wherein the actuator comprises a retaining member configured to interact with a mating retaining part on the plunger rod when the actuator sleeve is coaxially surrounding the retaining member and when the actuator and the actuator sleeve are in the locked and released positions, such that the plunger rod in a distal end position is secured from axial movement relative the actuator.

12. The medicament delivery device of claim 11, wherein the actuator sleeve, when the actuator and the actuator sleeve are in the released position, is configured to be axially moveable relative to the actuator between a first position, in which the plunger rod is secured in the distal end position, and a second position, in which the actuator releases the plunger rod.

13. The medicament delivery device of claim 12, wherein the retaining member of the actuator is configured to be disengaged from the mating retaining part on the plunger rod when the actuator sleeve is in the second position.

14. The medicament delivery device of claim 11, wherein the retaining member is radially outwardly biased.

15. The medicament delivery device of claim 8, wherein a shoulder extends from a distal wall of the securing compartment.

16. The medicament delivery device of claim 1, wherein the medicament delivery device is an auto-injector.

* * * * *